United States Patent
Yagi et al.

(10) Patent No.: US 11,529,045 B2
(45) Date of Patent: Dec. 20, 2022

(54) ENCOSCOPE-CLEANING DEVICE

(71) Applicant: Toray Industries, Inc., Tokyo (JP)

(72) Inventors: Toshihiko Yagi, Otsu (JP); Shoji Yabuzaki, Tokyo (JP)

(73) Assignee: Toray Industries, Inc., Tokyo (JP)

( * ) Notice: Subject to any disclaimer, the term of this patent is extended or adjusted under 35 U.S.C. 154(b) by 666 days.

(21) Appl. No.: 16/484,521

(22) PCT Filed: Feb. 9, 2018

(86) PCT No.: PCT/JP2018/004612
§ 371 (c)(1),
(2) Date: Aug. 8, 2019

(87) PCT Pub. No.: WO2018/147415
PCT Pub. Date: Aug. 16, 2018

(65) Prior Publication Data
US 2020/0029797 A1   Jan. 30, 2020

(30) Foreign Application Priority Data

Feb. 13, 2017   (JP) .............................. JP2017-024165

(51) Int. Cl.
*A46B 9/06* (2006.01)
*A61B 1/12* (2006.01)
*A61L 2/16* (2006.01)

(52) U.S. Cl.
CPC ................. *A61B 1/122* (2013.01); *A46B 9/06* (2013.01); *A61L 2/16* (2013.01); *A46B 2200/3013* (2013.01); *A61L 2202/24* (2013.01)

(58) Field of Classification Search
CPC .. A46B 5/00; A46B 5/02; A46B 9/021; A61B 1/122
See application file for complete search history.

(56) References Cited

U.S. PATENT DOCUMENTS

| | | | |
|---|---|---|---|
| 5,555,716 A  * | 9/1996 | Dugan | ..................... D02G 3/36 57/224 |
| 6,699,331 B1 | 3/2004 | Kritzler | |
| 2003/0213074 A1 | 11/2003 | Kawazoe et al. | |
| 2006/0191087 A1* | 8/2006 | Maguire | ................ A61B 90/70 15/104.16 |

(Continued)

FOREIGN PATENT DOCUMENTS

| | | |
|---|---|---|
| JP | 11-197092 A | 7/1999 |
| JP | 2004-24842 A | 1/2004 |

(Continued)

OTHER PUBLICATIONS

The Second Office Action dated Nov. 2, 2021, of counterpart Chinese Application No. 201880010693.9, along with an English translation.

(Continued)

*Primary Examiner* — Michael D Jennings
(74) *Attorney, Agent, or Firm* — DLA Piper LLP (US)

(57) ABSTRACT

An endoscope-cleaning device ensures effective cleaning of an endoscope. The endoscope-cleaning device includes a long flexible core member inserted into a twisted tubular body including a weft yarn including a microfiber yarn, wherein the microfiber yarn is made of polyester and the tubular body is twisted at 5 twists/5 cm to 15 twists/5 cm.

5 Claims, 2 Drawing Sheets

(56) References Cited

U.S. PATENT DOCUMENTS

| | | | |
|---|---|---|---|
| 2008/0028554 A1* | 2/2008 | Chu | B25G 1/102 |
| | | | 15/105 |
| 2014/0237748 A1* | 8/2014 | Sweeney | B08B 9/043 |
| | | | 15/210.1 |
| 2014/0250614 A1 | 9/2014 | Pisacane | |
| 2015/0059804 A1* | 3/2015 | Bergez | B32B 5/26 |
| | | | 15/118 |
| 2016/0158658 A1* | 6/2016 | Lakritz | A63H 3/16 |
| | | | 446/268 |
| 2021/0282540 A1* | 9/2021 | Serposi | A46B 5/02 |

FOREIGN PATENT DOCUMENTS

| | | |
|---|---|---|
| JP | 2010-506682 A | 3/2010 |
| JP | 2015-024105 A | 2/2015 |
| JP | 2015-077210 A | 4/2015 |
| KR | 10-1610760 | 4/2016 |
| WO | 2008/048823 A2 | 4/2008 |

OTHER PUBLICATIONS

Y. Gao et al., "Outdoor Costume Design Product Development," pp. 64 and 65, Mar. 2015, along with a partial English translation.
The Extended European Search Report dated Nov. 27, 2020, of counterpart European Application No. 18751628.1.
Notification of Reason for Refusal dated May 3, 2022, of counterpart Korean Patent Application No. 10-2019-7019718, along with an English translation.

\* cited by examiner

ENCOSCOPE-CLEANING DEVICE

TECHNICAL FIELD

This disclosure relates to a cleaning device for use with medical devices, and more specifically to a cleaning device for cleaning endoscopes.

BACKGROUND

During use in endoscopic examinations or surgical procedures, an endoscope typically becomes soiled with biological and other materials from a patient body (e.g., biliary fluids, saliva, feces, blood, pieces of tissue and the like) and potentially from other devices or materials used in conjunction with the endoscope. Because endoscopes are used multiple times, it is important that they are completely cleaned between uses to avoid cross-contamination between devices used with them, and between different patients.

A typical cleaning regimen for cleansing an endoscope includes wiping it down with a detergent (such as an enzymatic detergent), then soaking it in and flushing it with a same or different detergent, water, and air, and then finally drying it for sterilization. The detergent provides for chemical cleaning and the flushing provides for mechanical cleaning.

Some mechanical aids are known for use in cleaning the inner channels of an endoscope. For example, linear and tapered brushes having bristles projecting from a central shaft are known, but they disadvantageously provide abrasion to the luminal surfaces in the endoscope. As another example, U.S. Pat. No. 6,699,331 discloses a sponge device that spreads luminal contamination of an endoscope into a substantially uniform film on the luminal surface so that enzymatic cleaners can more efficiently and uniformly digest the contaminating material. However, the sponge device disclosed therein is not configured to provide the mechanical force needed to actually remove adhering luminal contaminants, but rather spreads them uniformly.

JP H11-197092 A proposes a cleaning device for automatic cleaning by brushing. That cleaning device has a plurality of brushes that movably connect to each other via a flexible yarn such as a fiber yarn. The cleaning device is inserted into the lumen of an endoscope and pushed forward by the pressure of cleaning water for brush cleaning of the inner surface of the lumen of the endoscope. However, during the brush cleaning, the tips of the bristles lightly and irregularly rub the inner surface of the lumen. Relatively easily removable dirt adhering to the inner surface of the lumen such as secretion (e.g., mucus), blood, tissue fragments, is removed by the cleaning, but microorganisms such as viruses, bacteria and others, are difficult to remove. The plurality of connected brushes may not contact the entire surface of the inner wall of the lumen, in particular, the inner surface with a scratch and/or the inner wall of the bending section or of the connecting section of different parts.

JP 2004-24842 A proposes a porous body for cleaning an endoscopic lumen for insertion of an endoscopic accessory. The porous body is an approximately spherical porous body formed of a large number of ultrafine fibers. The porous body is capable of swelling in the presence of an aqueous cleaning liquid so that the outer diameter of the porous body is larger than the inner diameter of the lumen to be cleaned by the porous body that has swelled. The porous body is also capable of being deformed for insertion into the lumen, and movable while maintaining contact with the inner wall of the lumen with an aid of an aqueous cleaning liquid flowing through the lumen. However, the porous body requires an aqueous cleaning liquid. In addition, although the main components of the dirt adhering to an endoscope are proteins and lipids, the porous body can only remove proteins, but not lipids.

It could therefore be helpful to provide an endoscope-cleaning device that ensures effective cleaning of an endoscope.

SUMMARY

We thus provide:
(1) An endoscope-cleaning device comprising a long flexible core member inserted into a twisted tubular body comprising a weft yarn comprising a microfiber yarn.
(2) The microfiber yarn is preferably made of polyester.
(3) The tubular body is preferably twisted at 5 twists/5 cm to 15 twists/5 cm.
(4) The microfiber yarn preferably has a diameter of 2 μm to 8 μm.

The endoscope-cleaning device comprises a twisted tubular body into which a long flexible core member is inserted and comprises a weft yarn comprising microfibers that effectively remove proteins and lipids adhering to the inner surface of an endoscope.

REFERENCE SIGNS LIST

Figure 1:
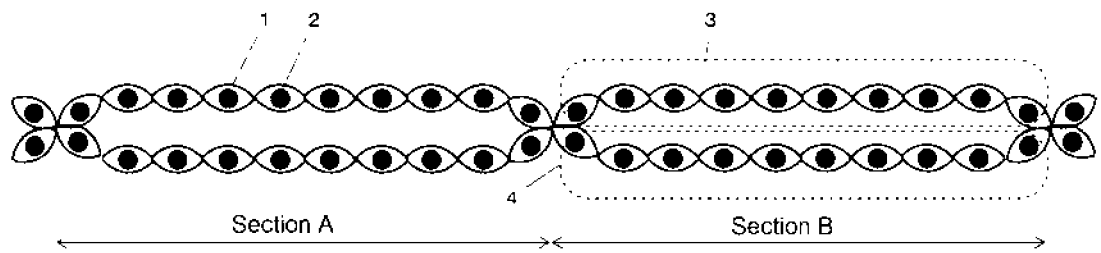
FIG. 1 is a sectional view showing an example of a double-layer woven fabric.

1 Warp yarn
2 Weft yarn
3 Face fabric
4 Back fabric
5 Tubular body
6 Core member
7 Microfiber yarn

DETAILED DESCRIPTION

Long Flexible Core Member

The core member can be made of a flexible material. The core member is, for example, made of a nylon. Various types of nylons are available, and any type of known nylons can be employed, including Nylon 6, Nylon 11, Nylon 12, Nylon 66 and the like. When the endoscope-cleaning device is used for an endoscope with an inner diameter of 3.2 mm, the core member preferably has an outer diameter of 1 mm to 2 mm and a length of 200 cm to 250 cm for ease of handling.

Tubular Body that Accommodates Inserted Core Member

The tubular body that accommodates the inserted core member may be a woven fabric or a knitted fabric, but is preferably a woven fabric. The weave for the woven fabric includes, for example, plain weave in which "each weft thread passes alternately over and under a warp thread and each warp thread passes alternately over and under a weft thread," twill weave in which "each weft thread does not pass alternately over and under a warp thread or vice versa, but each weft thread passes over one warp thread and then passes under two warp threads (1×2 twill), or each weft thread passes over one warp thread and then passes under three warp threads (1×3 twill)," satin weave in which "there are a small number of floats of weft threads and only warp threads appear to lie on the surface and therefore the fabric has a glossy surface," solidly covered weave that "uses colored threads to weave a background design on another type of weave such as a plain or satin weave," high density weave that "is the most suitable for and capable of reproducing fine detail that ordinary weave cannot produce such as an intricate artwork or small texts due to use of a special type of yarn or a high yarn density," shrink resistant weave that "resists shrinkage and distortion," and crepe weave that "produces a rough, dull surface like the skin of a pear" and the like. Of these, preferred is plain weave having more interlaced threads as compared to other types of weave and is therefore strong although thin as a fabric. The tubular body can be produced by weaving a fabric layer on one side and another fabric layer on the reverse side with the so-called hollow weave that can produce a hollow woven fabric in which fabric layers are joined at the selvage ends.

Tubular Body Made of Double-Layer Woven Fabric

Figure 2:
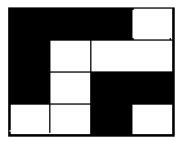
FIG. 2 is a weave diagram of the section A of the fabric of FIG. 1.
Figure 3:
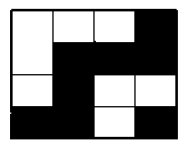
FIG. 3 is a weave diagram of the section B of the fabric of FIG. 1.

FIG. 1 is a sectional view showing an example of a double-layer woven fabric as an example of the tubular body. FIG. 2 is a weave diagram of the section A of the fabric of FIG. 1. FIG. 3 is a weave diagram of the section B of the fabric of FIG. 1. FIG. 1 contains a warp yarn 1, a weft yarn 2, a face fabric 3 on one side of the tubular body, and a back fabric 4 on the reverse side of the tubular body. The long flexible core member can be inserted between the face fabric 3 on one side of the tubular body and the back fabric 4 on the reverse side of the tubular body as shown in FIG. 1.

Weft Yarn

The weft yarn preferably contains a microfiber yarn. The microfiber yarn is prefer- ably an ultrafine fiber of about 2 to 8 μm in diameter. Typically, an oil film has a thickness of about 1 to 2 μm, and is impossible to wipe off with ordinary fibers, whose thickness is typically about 15 μm. However, the microfiber yarn of about 2 to 8 μm in diameter is capable of wiping off such an oil film. The weft yarn may contain a different yarn other than the microfiber yarn, and the diameter of the different yarn is preferably 10 to 20 μm but is not limited thereto.

Production Process of Microfiber

The microfiber may be produced by direct spinning process, sea-island spinning process, split or peeling spinning process, or ply spinning process. The sea-island spinning process has various advantages over the other three processes. For example, the sea-island spinning process can relatively easily produce any cross-sectional shape; the produced fibers are easily handled like ordinary fibers in high-order processing; and spacing between ultrafine fibers obtained after removal of the sea component is easily maintained in the woven fabric. The microfiber can be generated from, for example, an ultrafine fiber-generating fiber produced by melt spinning of polymers of an island component and a sea component containing a polyalkylene glycol.

Polymer that Constitutes Microfiber

The polymer that constitutes the microfiber is, for example, polyester, polyamide, polyolefin, polyphenylene sulfide or the like. Specific examples of polyester include polyethylene terephthalate, polybutylene terephthalate, polytrimethylene terephthalate and the like. Specific examples of polyamide include Nylon 6, Nylon 66, Nylon 12 and the like. The sea component of the sea-island type composite fiber may be polyethylene; polypropylene; polystyrene; a polyester copolymerized with sodium sulfoisophthalate, polyethylene glycol or the like; polylactic acid; or the like. A copolymerized polyester is preferred due to good spinnability, dissolvability and the like. The copolymerized polyester is preferably a polyester copolymerized with 5 to 10 mol % of sodium 5-sulfoisophthalate, and preferably further contains a polyalkylene glycol.

The polyalkylene glycol may be polyethylene glycol, polypropylene glycol, polybutylene glycol or the like. Polybutylene glycol is preferred because it is easy to handle, requires a reduced amount of an alkaline aqueous solution or the like, and has other advantages.

The microfiber may be generated from an ultrafine fiber-generating fiber as a precursor. The ultrafine fiber-generating fiber is, for example, a sea-island type composite fiber consisting of a sea component polymer and an island component polymer. The ultrafine fiber-generating fiber preferably contains a polyalkylene glycol in the sea component polymer serving as an easily dissolvable component. In the longitudinal section of the composite fiber, the polyalkylene glycol component preferably extends in the longitudinal direction and forms a stripe pattern.

The mass ratio of the poorly dissolvable component (the island component polymer) relative to that of the polyester-based easily dissolvable component (the sea component polymer) is preferably 0.2 to 0.8, and is more preferably 0.3 to 0.7. When the poorly dissolvable component is contained at a mass ratio of 0.2 or more, the amount of the polyester-based easily dissolvable component required to be removed is small, and consequently the productivity improves. When the poorly dissolvable component is contained at a mass ratio of 0.8 or less, the splittability of the poorly dissolvable component fibers improves, and also fusion of the poorly dissolvable component fibers is prevented.

The poorly dissolvable component (the island component polymer) is, for example, a polymer such as polyester, polyamide, polyolefin and polyphenylene sulfide. Specific examples of polyester include polyethylene terephthalate, polybutylene terephthalate, polytrimethylene terephthalate and the like. Specific examples of polyamide include Nylon 6, Nylon 66, Nylon 12 and the like.

The polyester-based easily dissolvable component refers to a component having 100-fold or higher solubility, preferably 200-fold or higher solubility, in a solvent such as an organic solvent or an aqueous solution such as an alkali solution, as compared with the poorly dissolvable component. Due to the 100-fold or higher difference in solubility, the poorly dissolvable component is protected from damage during the dissolving procedure, and the poorly dissolvable component is well dispersed.

The production process for the microfiber will be described below. The microfiber can be generated from, for example, an ultrafine fiber-generating fiber. The ultrafine fiber-generating fiber may be a sea-island type composite fiber containing two types of thermoplastic resins having different solubilities in a solvent or the like. The two types of thermoplastic resins serve as an island component polymer and a sea component polymer, respectively. The sea component polymer is removed by dissolving in a solvent or the like in post-processing, thereby converting the island component polymer into ultrafine fibers. Alternatively, the ultrafine fiber-generating fiber may be a peeling type composite fiber containing two types of thermoplastic resins that are alternately arranged in radial segments or in multilayer segments in the cross section of the fiber. The alternately arranged segments are then peeled or separated from each other so that the composite fiber is split into ultrafine fibers.

The sea-island type composite fiber may be a sea-island type composite fiber produced by spinning alternately arranged two types of components, i.e., the sea and island components, using a die for producing sea-island type composite fibers. Alternatively, the sea-island type composite fiber may be a blended spun fiber produced by spinning mixed two types of polymers, i.e., the sea and island component polymers. The sea-island type composite fiber is particularly preferred because ultrafine fibers of a uniform fineness and a sufficient length are obtained.

Number of Twisting of Tubular Body

The tubular body is preferably twisted at 5 twists/5 cm to 15 twists/5 cm. The tubular body twisted at less than 5 twists/5 cm will have poor cleaning effect, whereas the tubular body twisted at more than 15 twists/5 cm will have high resistance and tends to make cleaning difficult.

EXAMPLES

Our devices will be described in more detail with reference to Examples, but is not limited thereto. Various modifications and alterations are possible without departing from the technical scope of this disclosure.

1. Production of an Example of Endoscope-Cleaning Device

The weft yarn used was prepared as follows: a high shrinkage polyester yarn of 33 dtex and 6 filaments serving as a core was covered with two textured synthetic ultrafine microfiber yarns (sea-island composite type dissolution-splitting ultra-superfine polyester yarns) each of 66 dtex and 9 filaments, serving as a sheath and, then, the yarn was twisted together with two polyester yarns each of 55 dtex and 24 filaments at 130 T/m. The warp yarns used were two textured nylon yarns each of 56 dtex and 17 filaments. The weft yarn and the warp yarns were used to produce a tubular double-layer woven fabric of which the center portion was woven with plain weave. A Nylon 6 monofilament of 1.3 mm in diameter was inserted into the tubular double-layer woven fabric. In this manner, an example of an endoscope-cleaning device as shown in FIG. 4 was obtained.

Figure 4:
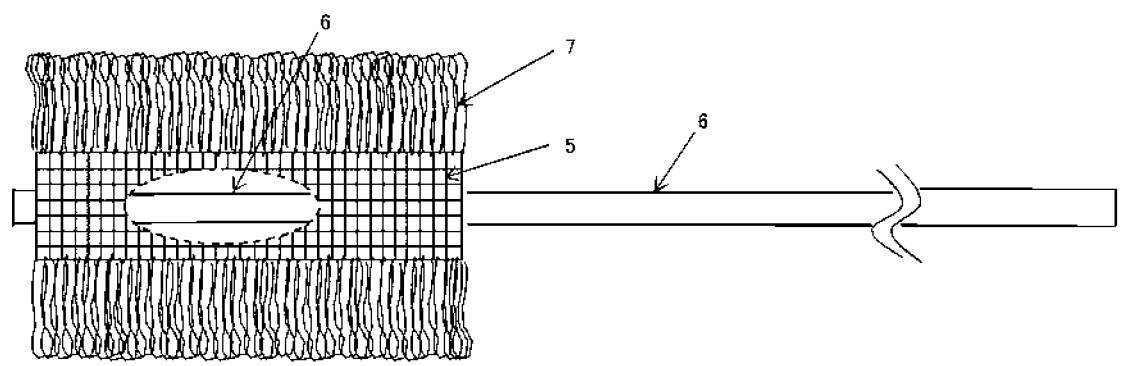
FIG. 4 is a partially broken plan view showing an example of an endoscope-cleaning device.
Figure 5:
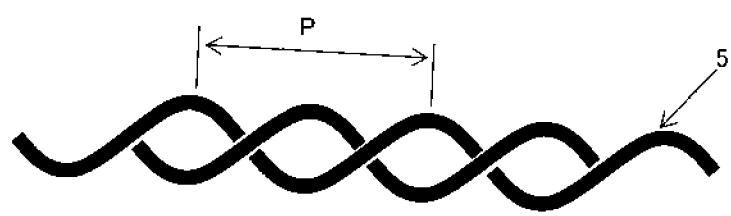
FIG. 5 is an enlarged view showing the twisting of the tubular body of an endoscope- cleaning device.

In FIG. 4, the tubular body made of the double-layer woven fabric is indicated by the numeral 5, the long flexible core member, made of the Nylon 6 monofilament, inserted into the tubular body is indicated by the numeral 6, and the microfiber yarns contained in the weft yarn of the tubular body are indicated by the numeral 7. The long flexible core member 6 made of the Nylon 6 monofilament was bonded with the tubular body 5 by ultrasonic fusion bonding. In FIG. 5, one twist pitch length is indicated by P. The tubular body 5 is preferably provided with twisting of 5 pitches to 15 pitches per 5 cm, most preferably 8 pitches per 5 cm.

2. Endoscope-Cleaning Device of Comparative Example

A brush having nylon bristles of 100 μm in diameter and 5 mm in length was attached to an end of a long, round stainless steel rod of about 1.5 mm in diameter, and was used as an endoscope-cleaning device of Comparative Example.

3. Evaluation of Dirt Removing Capacity
3-1 Removal Capacity for Proteins and Lipids
(1) Tube for evaluation test A polytetrafluoroethylene tube of 3 mm in inner diameter and 2 m in length was used as a tube for evaluation test.
(2) Pseudo-dirt For preparation of pseudo-dirt, bovine serum albumin, pig mucin and pure lard were mixed at a protein:lipid ratio of about 1:1 part by weight.

(3) Adherence of pseudo-dirt

The pseudo-dirt was injected into the tube for evaluation test using a micropipette, and the tube was swung right and left 20 times to allow the pseudo-dirt to adhere to the inner surface of the tube so that the thickness of the pseudo-dirt was approximately uniform.
(4) Cleaning and removal of pseudo-dirt Into the tube for evaluation test to which the pseudo-dirt was adhered, 200 mL of an alkaline detergent heated to 40° C. was injected using a 30 mL syringe. While the alkaline detergent was retained in the tube, the endoscope-cleaning device was inserted into the tube and then withdrawn to wipe the pseudo-dirt. Then, 200 mL of tap water heated to 40° C. was injected into the tube using a different 30 mL syringe and, then, the tap water was removed. Air was then injected into the tube three times using a different 30 mL syringe.

Using a tube for evaluation test and pseudo-dirt prepared in the same manner as above, the pseudo-dirt was allowed to adhere to the tube then the tube was cleaned in the same manner as above, and the adhering pseudo-dirt was wiped with the endoscope-cleaning device of Comparative Example.
(5) Evaluation of protein removing capacity The initial amount of the protein in the pseudo-dirt was determined as follows. Prior to injection of the alkaline detergent in the above procedure, 0.5 mL (milliliters) of the pseudo-dirt adhering to the inner surface of the above tube for evaluation test was collected. The protein was quantified by the Lowry method, which is a commonly used analysis method for quantifying proteins in which copper sulfate was added to a protein solution under alkaline conditions, then, Folin-Ciocalteu reagent was added to react, and the absorbance at 750 nm measured. The results are shown in Table 1 below as the initial amount of the protein.

Then, 0.5 mL of the pseudo-dirt adhering to the inner surface of the tube for evaluation test after the air injection procedure was collected, and the protein quantified by the Lowry method. The results are shown in Table 1 below. The amount of the protein shown in Table 1 is expressed in μg/mL.
(6) Evaluation of lipid removing capacity The initial amount of the lipid in the pseudo-dirt was determined as follows. Prior to injection of the alkaline detergent in the above procedure, 5 mL of the pseudo-dirt adhering to the inner surface of the above tube for evaluation test was collected. The dirt component was extracted with a mixed solvent containing chloroform and methanol at a volumetric ratio of 2:1, and dehydration performed to remove the solvent. The lipid was quantified by the gravimetric method. The results are shown in Table 2 below as the initial amount of the lipid.

Then, 5 mL of the pseudo-dirt adhering to the inner surface of the tube for evaluation test after the air injection procedure was collected. The dirt component was extracted with a mixed solvent containing chloroform and methanol at a volumetric ratio of 2:1, and dehydration performed to remove the solvent. The lipid was quantified by the gravimetric method. The results are shown in Table 2 below. The amount of the lipid shown in Table 2 is expressed in mg/mL.

TABLE 1

|  | Initial amount of protein | Endoscope-cleaning device | Endoscope-cleaning device of Comparative Example |
| --- | --- | --- | --- |
| No. 1 | 690 | <4 | <4 |
| No. 2 | 400 | <4 | <4 |
| No. 3 | 720 | <4 | <4 |

TABLE 1-continued

|  | Initial amount of protein | Endoscope-cleaning device | Endoscope-cleaning device of Comparative Example |
|---|---|---|---|
| No. 4 | 550 | <4 | <4 |
| No. 5 | 720 | <4 | <4 |
| Mean value | 616 | <4 | <4 |

TABLE 2

|  | Initial amount of lipid | Endoscope-cleaning device | Endoscope-cleaning device of Comparative Example |
|---|---|---|---|
| No. 1 | 5.5 | <0.1 | 1 |
| No. 2 | 5.9 | <0.1 | 1.2 |
| No. 3 | 4.7 | <0.1 | 1.3 |
| No. 4 | 5.7 | <0.1 | 0.7 |
| No. 5 | 5.2 | <0.1 | 1 |
| Mean value | 5.4 | <0.1 | 1.04 |

As shown in Tables 1 and 2, both the endoscope-cleaning devices and of Comparative Example exhibited comparable protein removing capacity, but our endoscope-cleaning device exhibited superior lipid removing capacity as compared to the Comparative Example.

3-2 ATP (Adenosine Triphosphate) Removing Capacity (1) ATP is an essential energy substance for every organism. ATP is contained in dirt derived from microorganisms or organisms and, therefore, the measurement of the amounts of ATP and AMP (adenosine monophosphate), which is a decomposition product of ATP, contained in a microbe-removing wiping cloth objectively confirms the contamination by organisms. The measurement is performed using, for example, a luminescent reagent containing firefly luciferase, luciferin, and pyruvate orthophosphate dikinase (PPDK). Firefly luciferase produces luminescence in the presence of ATP and luciferin. This reaction also produces AMP. The AMP is converted into ATP by PPDK and again subjected to the reaction with the luminescent reagent. In this manner, the luminescence corresponding to the total amount of ATP is obtained. The intensity of the luminescence is then measured with a particular measuring device to determine the degree of dirt.

(2) Tube for evaluation test

A polytetrafluoroethylene tube of 3 mm in inner diameter and 2 m in length was used as a tube for evaluation test.

(3) Pseudo-dirt

Pseudo-dirt was prepared as follows. A sewing machine oil (mineral oil) produced by Sumico Lubricant Co., Ltd. was mixed with an ATP (adenosine triphosphate) reagent produced by Wako Pure Chemical Industries, Ltd. so that the concentration of ATP was 0.001% by weight. The mixture was placed in an appropriate container, and uniformly agitated by ultrasonic vibration for 5 minutes to allow the ATP to uniformly disperse in the oil. The thus prepared mixture was used as pseudo-dirt.

(4) Adherence of pseudo-dirt

An amount of 20 μL of the pseudo-dirt was injected into the tube for evaluation test using a micropipette so that the thickness of the pseudo-dirt was approximately uniform.

(5) Removal of pseudo-dirt

While the pseudo-dirt was retained in the tube for evaluation test, the endoscope-cleaning device was inserted into the tube and then withdrawn to wipe the pseudo-dirt.

Using a tube for evaluation test and pseudo-dirt that were prepared in the same manner as above, the pseudo-dirt was allowed to adhere to the tube in the same manner as above, and the adhering pseudo-dirt was wiped with the endoscope-cleaning device of Comparative Example.

(6) Evaluation of ATP removing capacity

The initial ATP value in the pseudo-dirt was determined as follows. Prior to insertion of the endoscope-cleaning device into the tube for evaluation test to which the pseudo-dirt was adhered, the tube was split into two pieces, and the pseudo-dirt wiped with a sampling swab (trade name: "LuciPac Pen") moistened with 0.05 g of sterile purified water under a wiping load of about 100 g.

The endoscope-cleaning device was inserted into another tube for evaluation test to which the pseudo-dirt was adhered in the same manner as above and, then, the endoscope-cleaning device was withdrawn. The tube for evaluation test was split into two pieces, and the pseudo-dirt wiped with a sampling swab (trade name: "LuciPac Pen") moistened with 0.05 g of sterile purified water under a wiping load of about 100 g.

In the evaluation test of ATP removing capacity, the tube for determining the initial ATP value in the pseudo-dirt was separately prepared by adhering the pseudo-dirt to the tube for evaluation test in the same manner as above.

(7) Measurement of ATP value

The sampling swab used to wipe the pseudo-dirt was immersed in an extraction reagent (a surfactant (benzalkonium chloride)) to extract ATP. The extracted ATP was reacted with a luminescent reagent containing firefly luciferase, luciferin and pyruvate orthophosphate dikinase to produce luminescence. The intensity of the luminescence was measured with a luminescence meter (for example, "Lumitester PD-20" (trade name) produced by Kikkoman Biochemifa Company). The value of the ATP level in the dirt substance as measured with the luminescence meter was expressed as relative luminescence units (RLU). A lower RLU value indicates a smaller amount of ATP. The measurement results are shown in Table 3 below.

TABLE 3

|  | Initial ATP value | Endoscope-cleaning device | Endoscope-cleaning device of Comparative Example |
|---|---|---|---|
| No. 1 | 32015 | 50 | 29628 |
| No. 2 | 29320 | 57 | 31057 |
| No. 3 | 31748 | 68 | 33629 |
| No. 4 | 33817 | 49 | 28104 |
| No. 5 | 28721 | 71 | 30472 |
| Mean value | 31124 | 59 | 30578 |

As shown in Table 3, the endoscope-cleaning device exhibited far superior ATP removing capacity as compared with that of Comparative Example.

3-3 ADP (Adenosine Diphosphate) Removing Capacity (1) Based on the fact that raw meat contains a lot of ADP, dirt removing capacity can be determined by measuring the ability to wipe ADP, in addition to ATP and AMP.

(2) Tube for evaluation test

A polytetrafluoroethylene tube of 3 mm in inner diameter and 2 m in length was used as a tube for evaluation test.

(3) Aqueous ADP solution

An ADP (adenosine diphosphate) reagent produced by Wako Pure Chemical Industries, Ltd. was prepared to a concentration of 0.00001% (0.1 ppm) in ultrapure water.

(4) Adherence of aqueous ADP solution

An amount of 20 μL of the aqueous ADP solution was injected into the tube for evaluation test using a micropipette.

(5) Removal of aqueous ADP solution

While the aqueous ADP solution was retained in the tube for evaluation test, the endoscope-cleaning device was inserted into the tube and then withdrawn to wipe the aqueous ADP solution.

Using a tube for evaluation test and an aqueous ADP solution that were prepared in the same manner as above, the aqueous ADP solution was allowed to adhere to the tube in the same manner as above, and the adhering aqueous ADP solution was wiped with the endoscope-cleaning device of Comparative Example.

(6) Evaluation of ADP removing capacity

The initial ADP value in the aqueous ADP solution was determined as follows. Prior to insertion of the endoscope-cleaning device into the tube for evaluation test to which the aqueous ADP solution was adhered, the tube was split into two pieces, and the aqueous ADP solution wiped with a sampling swab (trade name: "LuciPac A3 Surface") moistened with 0.05 g of sterile purified water under a wiping load of about 100 g.

The endoscope-cleaning device was inserted into another tube for evaluation test to which the aqueous ADP solution was adhered in the same manner as above and, then, the endoscope-cleaning device was withdrawn. The tube for evaluation test was split into two pieces, and the aqueous ADP solution wiped with a sampling swab (trade name: "LuciPac A3 Surface") moistened with 0.05 g of sterile purified water under a wiping load of about 100 g.

In the evaluation test of aqueous ADP solution removing capacity, the tube for determining the initial ADP value in the aqueous ADP solution was separately prepared by adhering the aqueous ADP solution to the tube for evaluation test in the same manner as above.

(7) Measurement of ADP value

In the same manner as above (paragraph [0050] in WO 2018/147415), the luminescence corresponding to the amount of ADP was measured with a luminescence meter (for example, "Lumitester PD-20" (trade name) produced by Kikkoman Biochemifa Company), and expressed as relative luminescence units (RLU). A lower RLU value indicates a smaller amount of ADP. The measurement results are shown in Table 4 below.

TABLE 4

|  | Initial ADP value | Endoscope-cleaning device | Endoscope-cleaning device of Comparative Example |
| --- | --- | --- | --- |
| No. 1 | 12822 | 101 | 11618 |
| No. 2 | 11933 | 68 | 10411 |
| No. 3 | 13399 | 57 | 12872 |
| No. 4 | 12451 | 72 | 11369 |
| No. 5 | 13706 | 84 | 10706 |
| Mean value | 12862 | 76 | 11395 |

As shown in Table 4, our endoscope-cleaning device exhibited far superior ADP removing capacity as compared to the Comparative Example.

INDUSTRIAL APPLICABILITY

Our devices are useful as an endoscope-cleaning device.

The invention claimed is:

1. An endoscope-cleaning device comprising a long flexible core member inserted inside a twisted tubular woven fabric comprising a weft yarn comprising a microfiber yarn having a diameter of 2 μm to 8 μm.

2. The endoscope-cleaning device according to claim 1, wherein the microfiber yarn is made of polyester.

3. The endoscope-cleaning device according to claim 2, wherein the tubular body is twisted at 5 twists/5 cm to 15 twists/5 cm.

4. The endoscope-cleaning device according to claim 1, wherein the tubular body is twisted at 5 twists/5 cm to 15 twists/5 cm.

5. The endoscope-cleaning device according to claim 1, wherein a weave for producing the woven fabric is selected from the group consisting of plain weave, twill weave, satin weave, solidly covered weave, high density weave, shrink resistant weave and crepe weave.

* * * * *